(12) United States Patent
Osadchy et al.

(10) Patent No.: US 10,219,716 B2
(45) Date of Patent: Mar. 5, 2019

(54) USING A PIECEWISE-LINEAR MODEL OF A CATHETER ARM TO IDENTIFY CONTACT WITH TISSUE

(71) Applicant: Biosense Webster (Israel) Ltd., Yokneam (IL)

(72) Inventors: Daniel Osadchy, Haifa (IL); Meir Bar-Tal, Haifa (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 0 days.

(21) Appl. No.: 15/610,865

(22) Filed: Jun. 1, 2017

(65) Prior Publication Data

US 2018/0344187 A1 Dec. 6, 2018

(51) Int. Cl.
*A61B 5/00* (2006.01)
*A61B 5/042* (2006.01)
*A61B 5/06* (2006.01)

(52) U.S. Cl.
CPC ............ *A61B 5/0422* (2013.01); *A61B 5/063* (2013.01); *A61B 5/6852* (2013.01); *A61B 5/6859* (2013.01); *A61B 5/742* (2013.01); *A61B 5/6885* (2013.01); *A61B 5/6886* (2013.01)

(58) Field of Classification Search
CPC ...... A61B 5/0422; A61B 5/742; A61B 5/6852
See application file for complete search history.

(56) References Cited

U.S. PATENT DOCUMENTS

| 5,916,213 | A | 6/1999 | Haissaguerre |
| 6,370,412 | B1* | 4/2002 | Armoundas ........... A61B 5/042 |
| | | | 600/373 |
| 8,226,580 | B2 | 7/2012 | Govari |
| 8,456,182 | B2 | 6/2013 | Bar-Tal |
| 8,478,379 | B2 | 7/2013 | Osadchy |
| 9,615,764 | B2* | 4/2017 | Zino ....................... A61B 5/062 |
| 2007/0100332 | A1* | 5/2007 | Paul .................... A61B 18/1492 |
| | | | 606/41 |
| 2010/0121174 | A1* | 5/2010 | Osadchy .................. A61B 5/06 |
| | | | 600/409 |
| 2010/0160770 | A1 | 6/2010 | Govari |
| 2010/0292566 | A1 | 11/2010 | Nagano |
| 2011/0313417 | A1 | 12/2011 | De La Rama |
| 2012/0253167 | A1 | 10/2012 | Bonyak |
| 2012/0271145 | A1 | 10/2012 | Govari |
| 2016/0278856 | A1* | 9/2016 | Panescu ............... A61B 5/0422 |

* cited by examiner

*Primary Examiner* — Catherine M Voorhees
(74) *Attorney, Agent, or Firm* — Notaro, Michalos & Zaccaria P.C.

(57) ABSTRACT

Described embodiments include a method for use with a catheter that includes at least one flexible arm to which are coupled a plurality of electrodes. The method includes calculating, by a processor, respective estimated locations of the electrodes while the catheter is within a portion of a body of a subject, fitting a model of the catheter, which models the flexible arm as a piecewise-linear element that includes a plurality of linear segments, to the estimated locations, ascertaining for each of the electrodes, based on respective orientations of one or more of the linear segments per the fitting, whether the electrode is in contact with tissue of the subject, and updating a map of the portion of the body of the subject, in response to ascertaining that at least one of the electrodes is in contact with the tissue. Other embodiments are also described.

22 Claims, 3 Drawing Sheets

USING A PIECEWISE-LINEAR MODEL OF A CATHETER ARM TO IDENTIFY CONTACT WITH TISSUE

FIELD OF THE INVENTION

The present invention relates to the field of medical devices, and particularly to intracardiac catheters, such as those used for electroanatomical mapping.

BACKGROUND

U.S. Pat. No. 8,226,580 describes a method for operating a medical probe. The method includes pressing a distal end of the medical probe, which includes one or more arms that extend diagonally outward from a central shaft and have respective position transducers coupled thereto, against an intra-body surface, so as to cause the arms to exert pressure on the surface and bend with respect to the central shaft in response to the pressure. Positions of the respective position transducers coupled to the arms are measured, and the pressure exerted by the arms is estimated responsively to the measured positions.

U.S. Pat. No. 8,478,379 describes a method for visualization. The method includes receiving an input indicative of respective apparent coordinates of a plurality of points disposed along a length of a probe inside a body of a subject, and applying a model of known mechanical properties of the probe to the apparent coordinates so as to compute a cost function with respect to shapes that can be assumed by the probe in the body.

A shape is chosen responsively to the cost function, and corrected coordinates of the points along the length of the probe are generated based on the shape. The representation of the probe using the corrected coordinates is then displayed.

SUMMARY OF THE INVENTION

There is provided, in accordance with some embodiments of the present invention, a system for use with a catheter that includes at least one flexible arm to which are coupled a plurality of electrodes. The system includes an electrical interface and a processor configured to receive, via the electrical interface, a plurality of signals. The processor is further configured to calculate, from the received signals, respective estimated locations of the electrodes while the catheter is within a portion of a body of a subject. The processor is further configured to fit a model of the catheter, which models the flexible arm as a piecewise-linear element that includes a plurality of linear segments, to the estimated locations, to ascertain, for each electrode of the electrodes, based on respective orientations of one or more of the linear segments per the fitting, whether the electrode is in contact with tissue of the subject, and to update a map of the portion of the body of the subject, in response to ascertaining that at least one of the electrodes is in contact with the tissue.

In some embodiments, the piecewise-linear element includes at least three linear segments.

In some embodiments, the map is an electroanatomical map, and the processor is configured to update the electroanatomical map by incorporating information carried by an electrophysiological signal received from the at least one of the electrodes into the electroanatomical map.

In some embodiments, the processor is configured to update the map by incorporating a location of the at least one of the electrodes into the map.

In some embodiments, the processor is configured to ascertain whether the electrode is in contact with the tissue by:

calculating one or more deflection angles, each of which being formed by an intersection of a respective one of the linear segments, oriented per the fitting, with a respective other line, computing a deflection measure as a function of the deflection angles, and ascertaining whether the electrode is in contact with the tissue, by comparing the deflection measure to a threshold.

In some embodiments, the threshold is different for each of the electrodes.

In some embodiments, the deflection angles include an angle that is formed by an intersection of (i) one of the linear segments, to which, per the model, a proximalmost one of the electrodes is coupled, and (ii) a line along which the one of the linear segments was previously aligned.

In some embodiments, the one of the linear segments is a first one of the linear segments, and the deflection angles further include another angle, which is formed by an intersection of (i) a second one of the linear segments, which, per the model, is joined distally to the first one of the linear segments, and (ii) a line that distally extends the first one of the linear segments.

In some embodiments, the function varies between the electrodes.

In some embodiments, the deflection measure is a sum of the deflection angles, and the processor is configured to ascertain that the electrode is in contact with the tissue in response to the sum being greater than the threshold.

In some embodiments, the sum is a weighted sum that applies different respective weights to the deflection angles.

In some embodiments, the threshold is smaller for a more distal electrode, relative to a more proximal electrode.

There is further provided, in accordance with some embodiments of the present invention, a method for use with a catheter that includes at least one flexible arm to which are coupled a plurality of electrodes. The method includes calculating, by a processor, respective estimated locations of the electrodes while the catheter is within a portion of a body of a subject. The method further includes fitting a model of the catheter, which models the flexible arm as a piecewise-linear element that includes a plurality of linear segments, to the estimated locations. The method further includes ascertaining for each electrode of the electrodes, based on respective orientations of one or more of the linear segments per the fitting, whether the electrode is in contact with tissue of the subject, and updating a map of the portion of the body of the subject, in response to ascertaining that at least one of the electrodes is in contact with the tissue.

The present invention will be more fully understood from the following detailed description of embodiments thereof, taken together with the drawings, in which:

DETAILED DESCRIPTION OF EMBODIMENTS

Overview

Figure 1:
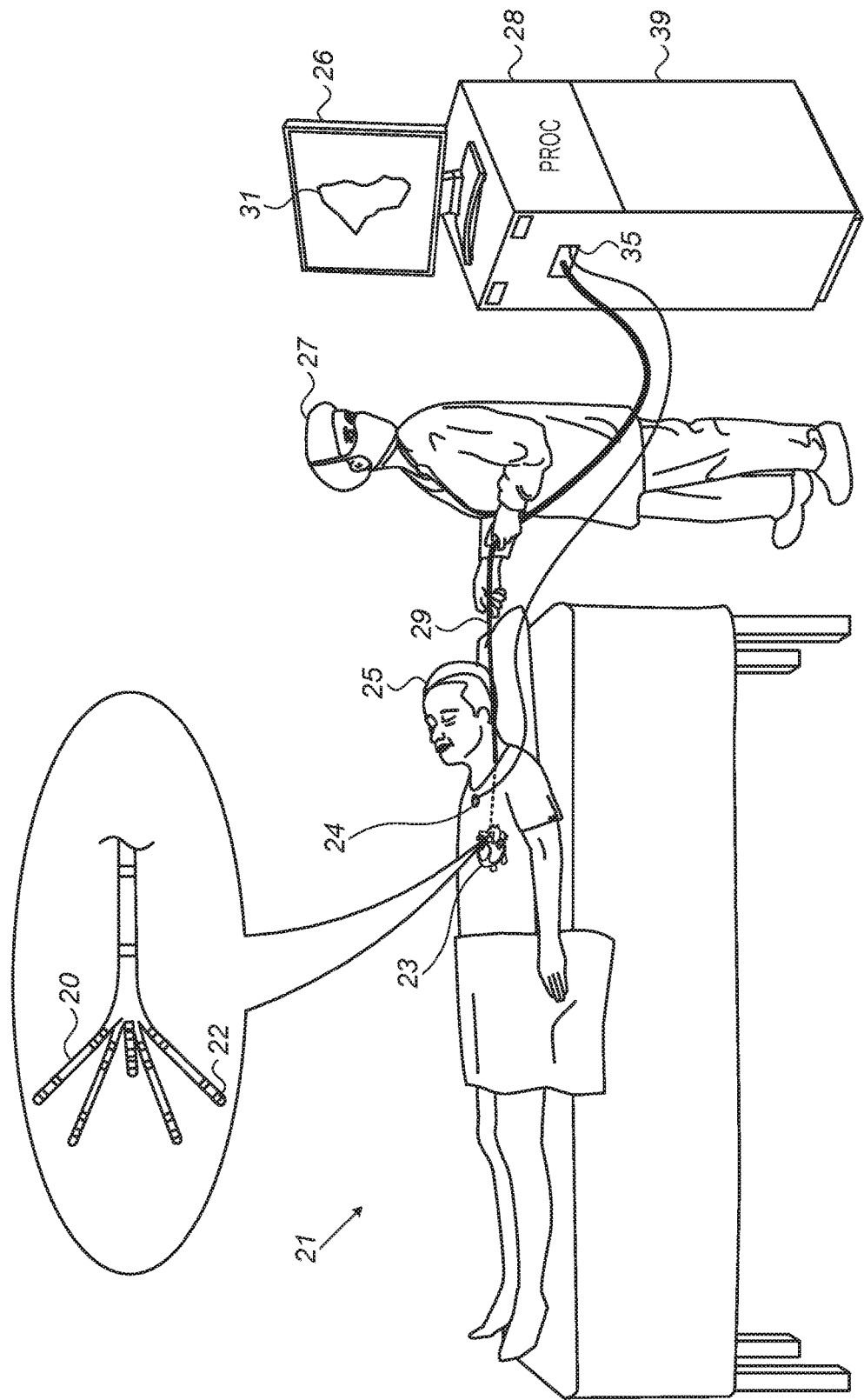
FIG. 1 is a schematic illustration of a system for electroanatomical mapping, in accordance with some embodiments of the present invention.

In embodiments of the present invention, a catheter comprising one or more flexible arms is inserted into a portion of a subject's body, such as the subject's heart. A plurality of electrodes coupled to the arms are then used to acquire electrophysiological signals, such as electrocardiographic (ECG) signals, from tissue of the subject. During the procedure, a tracking system is used to track the respective locations of the electrodes, such that each of the signals may be associated with the location at which the signal was acquired. For example, the Active Current Location (ACL) system, which is described in U.S. Pat. No. 8,456,182, whose disclosure is incorporated herein by reference, may be used. In the ACL system, a processor estimates the respective locations of the electrodes based on impedances measured between the electrodes and other, external electrodes that are coupled to the body of the subject.

A challenge, when performing such a procedure, is that it may not be apparent, at any given time, which of the electrodes is in contact with tissue of the subject. Thus, for example, it may be unclear whether the location of a given electrode, and/or any information carried by an electrophysiological signal received from the electrode, should be incorporated into the electroanatomical map under construction, given that the electrode may not actually be touching the tissue of the subject.

To address this challenge, embodiments of the present invention provide a method for ascertaining tissue contact. Per this method, the processor continually fits a model of the catheter (or at least of the electrode-comprising portion of the catheter) to the estimated electrode locations, such that, at any given time, the configuration of the model approximates the current configuration of the catheter (or at least of the electrode-comprising portion of the catheter). Upon one or more arms of the catheter contacting tissue of the subject, the configuration of the catheter changes, due to flexion of the arms. Hence, further to fitting the model to the estimated electrode locations, the processor may ascertain that one or more electrodes are contacting the tissue, based on the new configuration of the model.

Typically, each arm of the catheter is modeled as a piecewise-linear element having a plurality of linear segments. Given such a model, the processor may ascertain, for each of the electrodes on a given arm, whether the electrode is in contact with the tissue, based on the respective orientations, per the fitting, of the linear segments of the arm. For example, the processor may calculate one or more deflection angles, each of which (alone, or in combination with one or more other deflection angles) indicates the degree to which a respective one of the linear segments has been deflected from its previous, resting orientation. The processor may then compute a deflection measure as a function of these angles, and check for tissue contact by comparing the deflection measure to a particular threshold. For example, the processor may sum the deflection angles, and then ascertain tissue contact only if this sum is greater than the threshold.

System Description

Reference is initially made to FIG. 1, which is a schematic illustration of a system 21 for electroanatomical mapping, in accordance with some embodiments of the present invention.

FIG. 1 depicts a physician 27 using a catheter 29 to perform an electroanatomical mapping of a heart 23 of a subject 25. Catheter 29 comprises, at its distal end, one or more flexible arms 20, to each of which are coupled one or more electrodes 22. During the mapping procedure, electrodes 22 acquire electrophysiological signals, such as ECG signals, from the tissue of heart 23. A processor 28, typically located within a console 39, receives these signals via an electrical interface 35, which may comprise, for example, a port or socket, situated anywhere on the surface of, or inside, console 39. Processor 28 uses information contained in these signals to construct an electroanatomical map 31, which associates one or more electrophysiological properties of the heart with an anatomical model of the heart. During and/or following the procedure, processor 28 may display electroanatomical map 31 on a display 26.

During the procedure, the respective locations of electrodes 22 are tracked. Such tracking may be performed, for example, using the aforementioned ACL technique. Per this technique, a plurality of external electrodes 24 are coupled to the body of subject 25; for example, three external electrodes may be coupled to the subject's chest, and another three external electrodes may be coupled to the subject's back. (For ease of illustration, only one external electrode is shown in FIG. 1.) While electrodes 22 are inside the body of the subject, electric currents are continually passed between electrodes 22 and external electrodes 24, the resulting current amplitudes at external electrodes 24 are measured, and processor 28 receives, via electrical interface 35, signals that indicate these amplitudes. Based on the ratios between these amplitudes (or between the impedances implied by these amplitudes), and given the known positions of electrodes 24 on the subject's body, processor 28 continually calculates an estimated location of each of electrodes 22 within the subject's body.

Given the estimated location of any given electrode at any given time, the processor may use the estimated location, and/or an electrophysiological signal received from the electrode, to update the electroanatomical map. For example, the processor may incorporate the location of the electrode into the electroanatomical map, by updating the anatomical model that underlies the electroanatomical map to include the location of the electrode. Alternatively or additionally, the processor may extract an electrophysiological parameter (such as a local activation time) from the electrophysiological signal, and then associate this parameter with the portion of electroanatomical map 31 that corresponds to the estimated location of the electrode.

As noted above in the Overview, processor 28 is configured to ascertain whether a given electrode is in contact with the tissue, before incorporating the location of the electrode, and/or the signal received from the electrode, into the electroanatomical map. Techniques for such ascertaining are described hereinbelow, with reference to FIGS. 2 and 3.

In general, processor 28 may be embodied as a single processor, or as a cooperatively networked or clustered set of processors. Processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the processor in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Catheter Model

Figure 2:
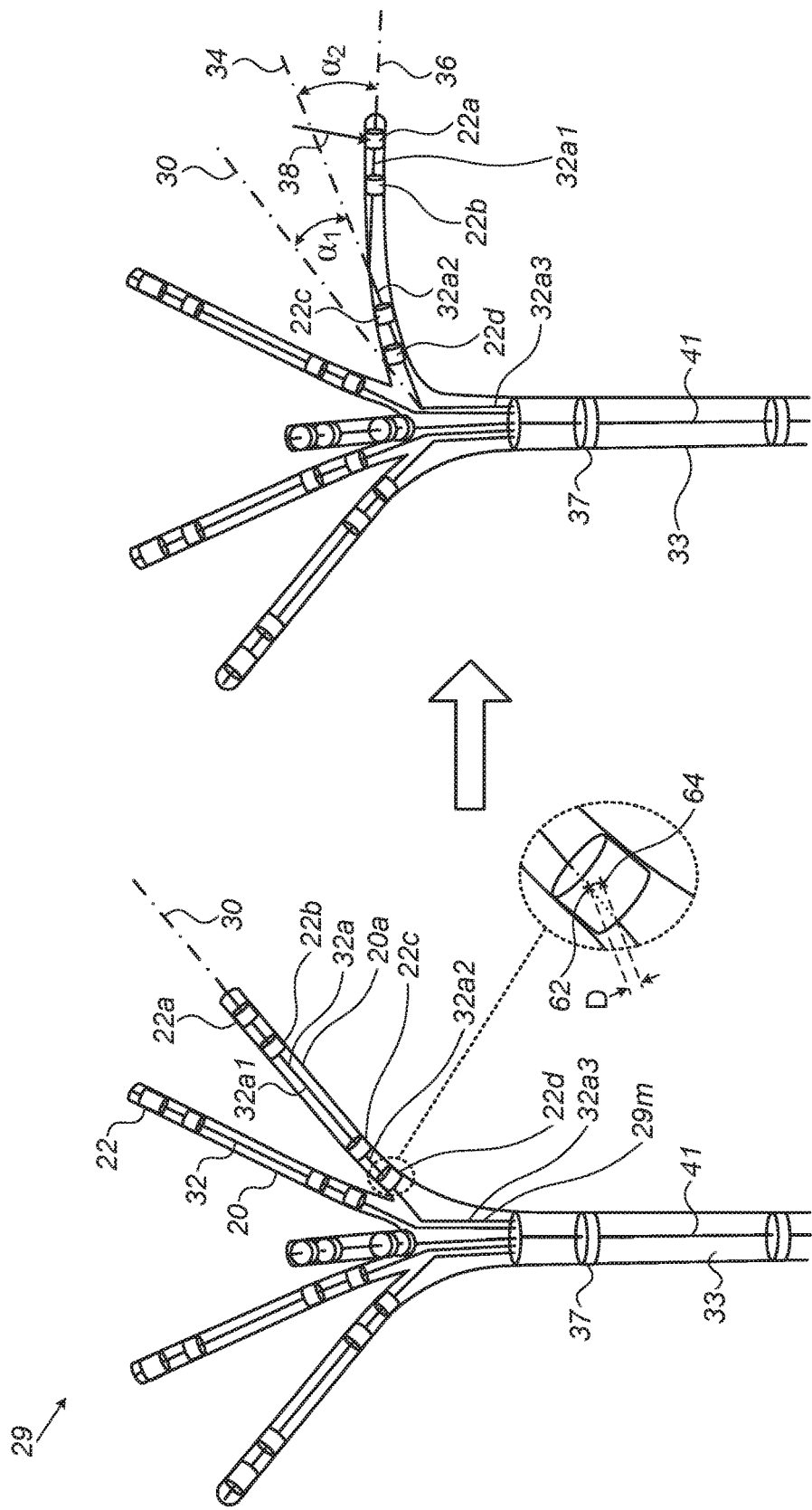
FIG. 2 is a schematic illustration of a technique used to ascertain contact of electrodes with tissue, in accordance with some embodiments of the present invention.

Reference is now made to FIG. 2, which is a schematic illustration of a technique used to ascertain contact of electrodes 22 with tissue, in accordance with some embodiments of the present invention.

The left side of FIG. 2 shows catheter 29 in its default (or "resting") configuration, which the catheter adopts in the absence of any external forces acting on the catheter. In the particular example shown, catheter 29 comprises five flexible arms 20, each of which protrudes obliquely from the central shaft 33 of the catheter. Notwithstanding this particular configuration, however, it is noted that the techniques described herein may be applied to any suitable catheter configuration having any number of flexible arms with any suitable orientations.

Superimposed on the catheter is a catheter model 29m, which is used by processor 28 to model the catheter. Catheter model 29m models each of the flexible arms of the catheter as a piecewise-linear element 32 that includes a plurality of (e.g., two, three, or more) linear segments. (Catheter shaft 33 is typically also modeled as a linear segment 41.) For example, in FIG. 2, a particular arm 20a of the catheter is modeled by a piecewise-linear element 32a. Linear element 32a includes three interconnected linear segments 32a1, 32a2, and 32a3, which collectively approximate the shape of arm 20a at any given time. In the particular example shown, the proximalmost linear segment 32a3 is parallel to the shaft of the catheter.

During the procedure, the processor continually calculates the estimated locations of electrodes 22 as described above, and then fits catheter model 29m to these estimated locations. The processor thus continually computes the current configuration of the model, which approximates the current configuration of the catheter arms. For example, to approximate the current configuration of arm 20a, the processor first calculates the respective estimated locations of the four electrodes 22a, 22b, 22c, and 22d that are coupled to arm 20a. The processor then fits the model to these estimated locations. For example, the processor may adjust, as necessary, the respective locations and/or orientations of linear segments 32a1 and 32a2, such that the distance between the estimated electrode locations and the locations of the electrodes on the linear segments (as assumed by the model) is minimized, as described, for example, in U.S. Pat. No. 8,478,379, whose disclosure is incorporated herein by reference.

By way of illustration, FIG. 2 shows, for electrode 22d, the estimated location 64 of the electrode as calculated by the processor, along with the location 62 of the electrode as assumed by the model. (Location 62 lies along linear segment 32a2.) To fit the model to the estimated electrode locations, the processor may apply a minimization algorithm that minimizes a distance function that takes into account the distance D between estimated location 64 and location 62, along with the analogous distances for the other electrodes.

Typically, at least one other electrode 37 is coupled to the distal portion of the catheter shaft, proximally to the arms. Based on the estimated location of this electrode, the processor may further establish the orientation of linear segment 32a3, which, as described above, is parallel to the catheter shaft.

Following the fitting of the model to the estimated electrode locations, the processor ascertains, for each of the electrodes, whether the electrode is in contact with tissue of the subject, based on the respective orientations, per the fitting, of one or more of the linear segments.

By way of illustration, the right side of FIG. 2 shows the configuration of catheter 29 upon arm 20a contacting tissue of the subject. As illustrated, the force 38 of contact causes arm 20a to deflect proximally. Due to this deflection, the configuration of element 32a, as computed by the processor by fitting the model to the estimated electrode locations, changes. In particular, linear segment 32a2, which was previously aligned with a first line (or "axis") 30, becomes aligned with a second line 34, while linear segment 32a1, which was also previously aligned with first line 30, becomes aligned with a third line 36. As described in detail below, given this new configuration, the processor may infer, from the new orientations of the linear segments, that at least some of the electrodes are in contact with tissue of the subject.

Tissue-Contact-Ascertaining Algorithm

The section below describes an algorithm that is used by processor 28, in some embodiments, to ascertain whether at least some of the electrodes on catheter 29 are in contact with tissue. This algorithm typically comprises two sub-algorithms: a first sub-algorithm for calculating one or more deflection angles for each arm of the catheter, and a second sub-algorithm for calculating one or more deflection measures from the deflection angles, and comparing these deflection measures to one or more suitable thresholds.

(i) Calculation of Deflection Angles

Typically, for each arm, the processor first quantifies the degree to which the arm has been deflected from its previous default orientation by calculating a plurality of deflection angles, each of which is formed by an intersection of a respective one of the linear segments, oriented per the fitting, with a respective other line. For example, the processor may calculate a first deflection angle $\alpha_1$, which is formed by the intersection of (i) linear segment 32a2, to which, per the model, the proximalmost one of the electrodes is coupled, and (ii) first line 30, along which linear segment 32a2 was previously aligned, prior to being deflected. (Line 30 may be identified by the processor as being oriented at a given angle with respect to segment 32a3, i.e., with respect to the shaft of the catheter.) The processor may further calculate a second angle $\alpha_2$, which is formed by the intersection of (i) linear segment 32a1, which, per the model, is joined distally to linear segment 32a2, and (ii) second line 34, which distally extends linear segment 32a2. (Since linear segment 32a1 was deflected by a total angle of $\alpha_1+\alpha_2$, second angle $\alpha_2$ indicates, in combination with first angle $\alpha_1$, the degree to which linear segment 32a1 was deflected.) Similarly, if there were another, more distal linear segment in piecewise-linear element 32a, the processor might also calculate the angle between this hypothetical linear segment and line 36.

(ii) Calculation of Deflection Measure(s), and Comparison to Threshold(s)

Next, the processor iterates through the electrodes on arm 20a. For each of the electrodes, the processor computes a deflection measure as a function of one or more of the deflection angles. Based on the deflection measure, the processor ascertains whether the electrode is in contact with tissue of the subject.

For example, the processor may compute a sum of the angles $\alpha_1$ and $\alpha_2$ (which, as described above, indicates the total deflection of the distalmost segment $32a1$), and ascertain that a given electrode is in contact with the tissue only if the sum is greater than a given threshold. In some embodiments, this sum is a weighted sum $(w_1\alpha_1+w_2\alpha_2)$ that applies different respective weights $w_1$ and $w_2$ to the angles, where each of the weights is greater than or equal to zero.

Typically, the threshold is different for each of the electrodes. For example, the threshold may be smaller for a more distal electrode, relative to a more proximal electrode. Thus, for example, to establish that electrode $22a$ and/or electrode $22b$ is in contact with tissue, the processor may require that $\alpha_1+\alpha_2$ be greater than only 15 degrees, while to establish that electrode $22c$ and/or electrode $22d$ is in contact with tissue, the processor may require that $\alpha_1+\alpha_2$ be greater than 30 degrees.

In some embodiments, the function varies between the electrodes (such that the deflection measure varies between the electrodes), alternatively or additionally to the threshold varying between the electrodes. For example, for electrode $22a$ and/or electrode $22b$, the processor may assign a low weighting to $w_1$, relative to $w_2$, in the weighted sum $w_1\alpha_1+w_2\alpha_2$, while for electrode $22c$ and/or electrode $22d$, the processor may assign a low weighting to $w_2$, relative to $w_1$.

In response to ascertaining that at least one of the electrodes is in contact with tissue, the processor may update the electroanatomical map, by incorporating the location of the electrode(s), and/or information carried by the signal(s) received from the electrode(s), into the electroanatomical map.

Flow Diagram

Figure 3:
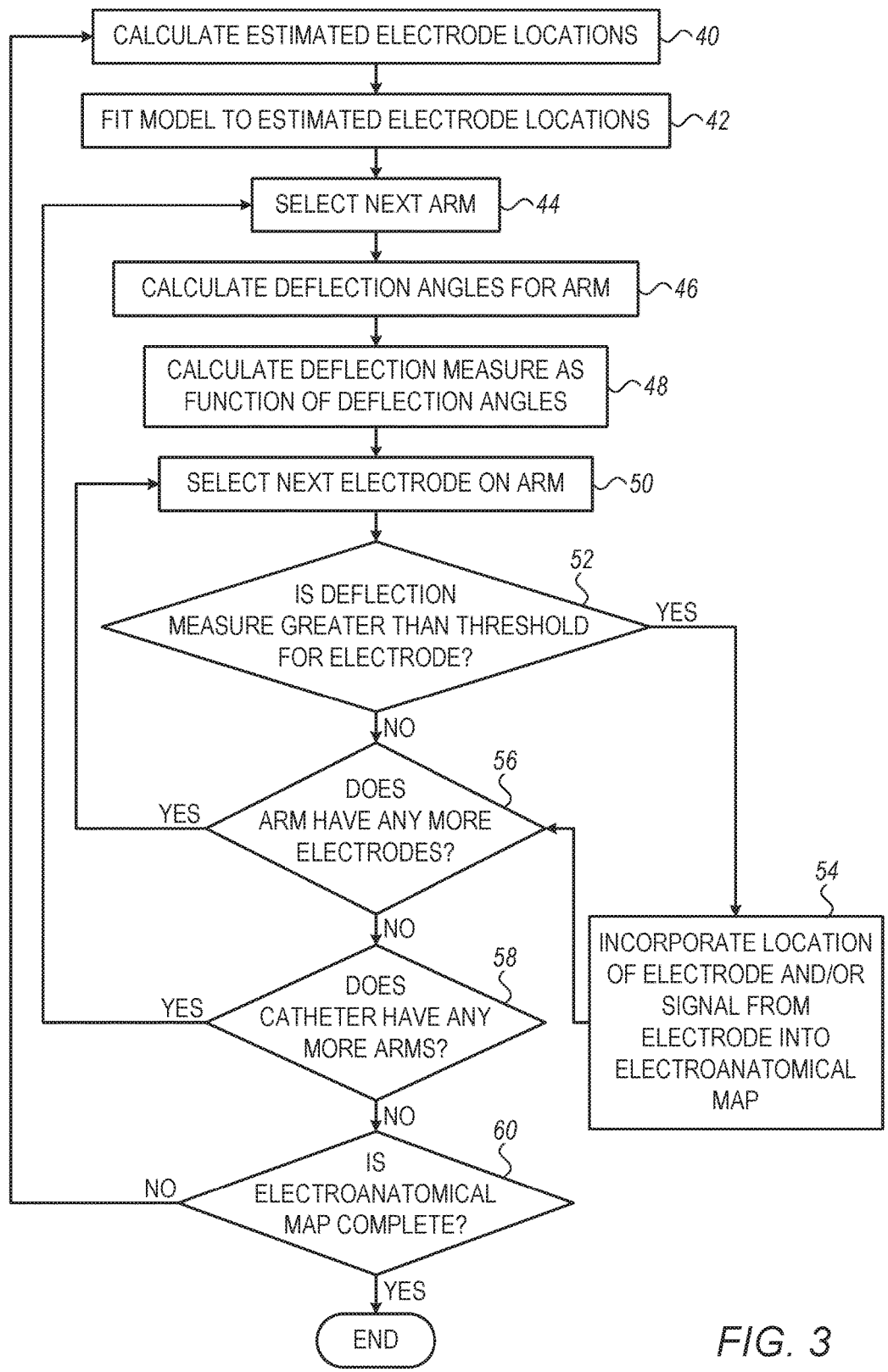
FIG. 3 is a flow diagram for a method for constructing an electroanatomical map, in accordance with some embodiments of the present invention.

Reference is now made to FIG. 3, which is a flow diagram for a method for constructing an electroanatomical map using the techniques described above with reference to FIG. 2, in accordance with some embodiments of the present invention. (FIG. 3 assumes that catheter 29 is already inside the heart of the subject.)

First, at a location-calculating step 40, the processor calculates the respective estimated locations of the electrodes on catheter 29. Next, at a fitting step 42, the processor fits a model, which, as described above, models each of the arms of the catheter as a piecewise-linear element, to these estimated locations. (Typically, as described above with reference to FIG. 2, the processor fits the model by applying a suitable minimization algorithm for minimizing the distances between the locations of the electrodes on the model and the estimated locations of the electrodes as calculated by the processor.) Next, at an arm-selecting step 44, the processor selects one of the catheter arms, to which the processor will apply the tissue-contact-ascertaining algorithm.

As described above, the tissue-contact-ascertaining algorithm typically comprises a first sub-algorithm for deflection-angle calculation, and a second sub-algorithm for deflection-measure calculation. Per the first sub-algorithm, the processor, at an angle-calculating step 46, calculates one or more deflection angles for the selected arm. As described above with reference to FIG. 2, these angles quantify the degree to which the arm has been deflected from its previous default orientation.

Next, per the second sub-algorithm, the processor, at a deflection-measure-calculating step 48, calculates a deflection measure as a function of the angles calculated at angle-calculating step 46. For example, as described above with reference to FIG. 2, the processor may calculate a sum—such as a weighted sum—of the angles. Subsequently, as further described immediately below, the processor iterates through the electrodes on the arm, checking each electrode for contact with tissue.

The processor begins each iteration by selecting an electrode, at an electrode-selecting step 50. Next, at a first checking step 52, the processor checks whether the deflection measure calculated at deflection-measure-calculating step 48 is greater than the threshold for the electrode. (As noted above, a separate threshold may be established for each electrode, in accordance with the position of the electrode on the arm.) If yes, the processor, at a map-updating step 54, updates the electroanatomical map, by incorporating the location of the electrode, and/or a signal received from the electrode, into the electroanatomical map. For example, the processor may add, to the map, a data point that associates electrophysiological information from the signal with the location of the portion of tissue that is in contact with the electrode.

Following map-updating step 54, or if the deflection measure is not greater than the threshold, the processor, at a second checking step 56, checks if the arm has any more electrodes that have not yet been checked for contact. If yes, the processor returns to electrode-selecting step 50, and selects the next electrode on the arm.

Following the iteration through the electrodes, the processor, at a third checking step 58, checks if the catheter has any more arms that have not yet been checked for contact. If yes, the processor returns to arm-selecting step 44, and selects the next arm of the catheter.

Following the iteration through the arms of the catheter, the processor, at a fourth checking step 60, checks if the electroanatomical map is complete. For example, the processor may check if the physician has provided an input indicating that the map is complete. If yes, the construction of the electroanatomical map ends. Otherwise, the processor returns to location-calculating step 40.

FIG. 3 assumes that the same function is used for all of the electrodes on a given arm, such that deflection-measure-calculating step 48 is performed only once for each arm. It is noted, however, that in alternative embodiments, deflection-measure-calculating step 48 may be repeatedly performed, using any number of different functions, such that a different respective measure is calculated for each of one or more of the electrodes on the arm.

Although the present description relates mainly to the electroanatomical mapping of a heart, it is noted that embodiments of the present invention may be applied to any anatomical mapping application. For example, using the techniques described herein, an anatomical map, which does not necessarily include any electrophysiological information, of any portion of a subject's body, may be constructed, by repeatedly adding to the map the location of any electrode that is determined to be in contact with tissue.

For anatomical mapping applications that do not require the acquisition of electrophysiological information, other types of sensors may be used in place of electrodes 22, with other types of tracking systems being used in place of the ACL tracking system. For example, the arms of the catheter may be fitted with electromagnetic sensors, and a magnetic field may be generated in the vicinity of the subject, such that the sensors output electric signals in the presence of the magnetic field. The processor may receive these signals via electrical interface 35, calculate the estimated locations of the sensors from these signals (as described, for example, in U.S. Pat. Nos. 5,391,199, 5,443,489, or US Patent Application Publication 2007/0265526, whose disclosures are incorporated herein by reference), and then use the techniques described herein to ascertain which of the sensors are in contact with tissue. In response to ascertaining that at least one of the sensors is in contact with tissue, the processor may incorporate the location of the sensor into the anatomical map.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for use with a catheter that includes at least one flexible arm to which are coupled a plurality of electrodes, the system comprising:
   an electrical interface; and
   a processor, configured:
      to receive, via the electrical interface, a plurality of signals,
      to calculate, from the received signals, respective estimated locations of the electrodes while the catheter is within a portion of a body of a subject,
      to fit a model of the catheter, which models the flexible arm as a piecewise-linear element that includes a plurality of linear segments, to the estimated locations,
      to ascertain, for each electrode of the electrodes, based on respective orientations of one or more of the linear segments per the fitting, whether the electrode is in contact with tissue of the subject, and
      to update a map of the portion of the body of the subject, in response to ascertaining that at least one of the electrodes is in contact with the tissue,
   wherein the processor is configured to ascertain whether the electrode is in contact with the tissue by:
      calculating one or more deflection angles, each of which being formed by an intersection of a respective one of the linear segments, oriented per the fitting, with a respective other line,
      computing a deflection measure as a function of the deflection angles, and
      ascertaining whether the electrode is in contact with the tissue, by comparing the deflection measure to a threshold.

2. The system according to claim 1, wherein the piecewise-linear element includes at least three linear segments.

3. The system according to claim 1, wherein the map is an electroanatomical map, and wherein the processor is configured to update the electroanatomical map by incorporating information carried by an electrophysiological signal received from the at least one of the electrodes into the electroanatomical map.

4. The system according to claim 1, wherein the processor is configured to update the map by incorporating a location of the at least one of the electrodes into the map.

5. The system according to claim 1, wherein the threshold is different for each of the electrodes.

6. The system according to claim 1, wherein the deflection angles include an angle that is formed by an intersection of (i) one of the linear segments, to which, per the model, a proximalmost one of the electrodes is coupled, and (ii) a line along which the one of the linear segments was previously aligned.

7. The system according to claim 6, wherein the one of the linear segments is a first one of the linear segments, and wherein the deflection angles further include another angle, which is formed by an intersection of (i) a second one of the linear segments, which, per the model, is joined distally to the first one of the linear segments, and (ii) a line that distally extends the first one of the linear segments.

8. The system according to claim 1, wherein the function varies between the electrodes.

9. The system according to claim 1, wherein the deflection measure is a sum of the deflection angles, and wherein the processor is configured to ascertain that the electrode is in contact with the tissue in response to the sum being greater than the threshold.

10. The system according to claim 9, wherein the sum is a weighted sum that applies different respective weights to the deflection angles.

11. The system according to claim 9, wherein the threshold is smaller for a more distal electrode, relative to a more proximal electrode.

12. A method for use with a catheter that includes at least one flexible arm to which are coupled a plurality of electrodes, the method comprising:
   calculating, by a processor, respective estimated locations of the electrodes while the catheter is within a portion of a body of a subject;
   fitting a model of the catheter, which models the flexible arm as a piecewise-linear element that includes a plurality of linear segments, to the estimated locations;
   based on respective orientations of one or more of the linear segments per the fitting, ascertaining, for each electrode of the electrodes, whether the electrode is in contact with tissue of the subject; and
   updating a map of the portion of the body of the subject, in response to ascertaining that at least one of the electrodes is in contact with the tissue,
   wherein ascertaining whether the electrode is in contact with the tissue comprises:
      calculating one or more deflection angles, each of which being formed by an intersection of a respective one of the linear segments, oriented per the fitting, with a respective other line;
      computing a deflection measure as a function of the deflection angles; and
      ascertaining whether the electrode is in contact with the tissue, by comparing the deflection measure to a threshold.

13. The method according to claim 12, wherein the piecewise-linear element includes at least three linear segments.

14. The method according to claim 12, wherein the map is an electroanatomical map, and wherein updating the electroanatomical map comprises updating the electroanatomical map by incorporating information carried by a signal received from the at least one of the electrodes into the electroanatomical map.

15. The method according to claim 12, wherein updating the map comprises updating the map by incorporating a location of the at least one of the electrodes into the map.

16. The method according to claim 12, wherein the threshold is different for each of the electrodes.

17. The method according to claim 12, wherein the deflection angles include an angle that is formed by an intersection of (i) one of the linear segments, to which, per the model, a proximalmost one of the electrodes is coupled, and (ii) a line along which the one of the linear segments was previously aligned.

18. The method according to claim 17, wherein the one of the linear segments is a first one of the linear segments, and wherein the deflection angles further include another angle, which is formed by an intersection of (i) a second one of the linear segments, which, per the model, is joined distally to the first one of the linear segments, and (ii) a line that distally extends the first one of the linear segments.

19. The method according to claim 12, wherein the function varies between the electrodes.

20. The method according to claim 12, wherein the deflection measure is a sum of the deflection angles, and wherein ascertaining whether the electrode is in contact with the tissue comprises ascertaining that the electrode is in contact with the tissue in response to the sum being greater than the threshold.

21. The method according to claim 20, wherein the sum is a weighted sum that applies different respective weights to the deflection angles.

22. The method according to claim 20, wherein the threshold is smaller for a more distal electrode, relative to a more proximal electrode.

* * * * *